(12) United States Patent
Thormaehlen et al.

(10) Patent No.: US 7,273,860 B2
(45) Date of Patent: Sep. 25, 2007

(54) METHOD AND PHARMACEUTICAL COMPOSITIONS FOR TREATING OR INHIBITING RENAL DYSFUNCTIONS, DISEASES OR DISORDERS, PARTICULARLY IN DIABETIC PATIENTS

(75) Inventors: Dirk Thormaehlen, Ronnenberg (DE); Berthold Hocher, Klein Machnow (DE); Harald Waldeck, Isernhagen (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 199 days.

(21) Appl. No.: 10/988,847

(22) Filed: Nov. 16, 2004

(65) Prior Publication Data

US 2005/0137183 A1     Jun. 23, 2005

Related U.S. Application Data

(60) Provisional application No. 60/523,106, filed on Nov. 19, 2003.

(30) Foreign Application Priority Data

Nov. 18, 2003   (EP) .................................. 03104264

(51) Int. Cl.
    *A61K 31/55* (2006.01)
(52) U.S. Cl. ................................. 514/212.07
(58) Field of Classification Search .............. None
    See application file for complete search history.

(56) References Cited

U.S. PATENT DOCUMENTS

| 5,677,297 A | 10/1997 | Waldeck et al. |
| 5,783,573 A | 7/1998 | Rozsa et al. |
| 6,482,820 B2 | 11/2002 | Wilkins et al. |
| 6,906,059 B2 * | 6/2005 | Rozsa et al. ........... 514/212.07 |

FOREIGN PATENT DOCUMENTS

| DE | 195 10 566 A1 | 3/1995 |
| EP | 0 733 642 A1 | 3/1996 |
| WO | WO 00/48601 | 8/2000 |
| WO | WO 01/03699 A1 | 1/2001 |
| WO | WO 01/15673 A2 | 3/2001 |
| WO | WO 03/059939 A1 | 7/2003 |
| WO | WO 03/097067 A1 | 11/2003 |

OTHER PUBLICATIONS

"Combined inhibition of neutral endopeptidase with angiotensin converting enzyme or endothelin converting enzyme in experimental diabetes", Iikka Tikkanen et al; Journal of Hypertension 2002, vol. 20, No. 4, pp. 707-714.

"Effects of Endothelin Receptor Antagonists on the Progression of Diabetic Nephropathy", Berthold Hocher et al; Nephron 2001; 87; pp. 161-169.

"Renal Endothelin System in Diabetes: Comparison of Angiotensin-Converting Enzyme Inhibition and Endothelin-A Antagonism"; Berthold Hocher et al; Journal of Cardiovascular Pharmacology; 31 (Supp 1) pp. 5492-5495; 1998.

(SLV-306) "Antihypertensive Treatment of Hear tFailure Neprilysin Inhibitor Endothelin-Converting Enzyme Inhibitor" I.A. Sorbera et al; Drugs of the Future 2002 27(1) p. 27-31.

"Urinary Protein as Measured with a Pyrogallot Red-Molybdate Complex, Manually and in a Hitachi 726 Automated Analyzer"; Nobuko Watanabe et al; Clinical Chemistry, vol. 32, No. 8, 1986, pp. 1551-1544.

Partial European Search Report, for EP 03 10 4264, Mar. 17, 2004.

* cited by examiner

*Primary Examiner*—Raymond J Henley, III
(74) *Attorney, Agent, or Firm*—Crowell & Moring LLP

(57) ABSTRACT

Treatment and/or inhibition of renal dysfunction, disease or disorder in larger mammals, and particularly in humans, especially in human patients suffering from diabetes, using benzazepine-N-acetic acid derivatives which contain an oxo-group in the α-position to the nitrogen atom and are substituted in position 3 by a 1-(carboxyalkyl)cyclopentyl-carbonylamino radical, and/or salts or biolabile esters or physiologically acceptable solvates thereof, and production of pharmaceutical compositions and products suitable for treatment and/or inhibition of renal dysfunction, disease or disorder, particularly in diabetic patients, but also in patients with syndrome X or in patients with a renal dysfunction, disease and/or disorder, which patients are additionally hypertensive, obese, hyperglycemic and/or subject to a metabolic disorder.

12 Claims, 2 Drawing Sheets

Fig. 1
Proteinuria
Fig. 1 A
12 Weeks
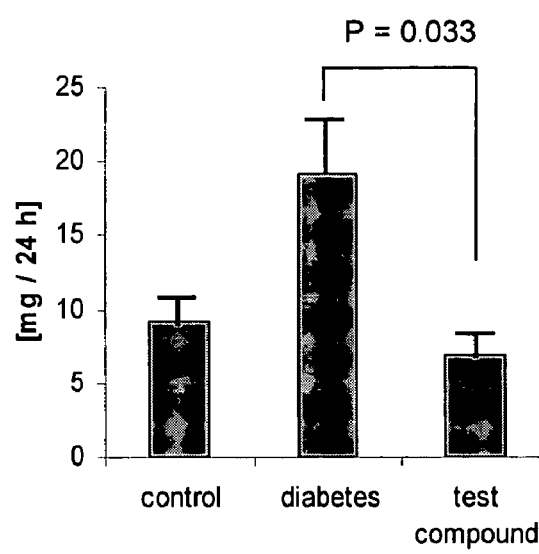
Fig. 1 B
18 Weeks
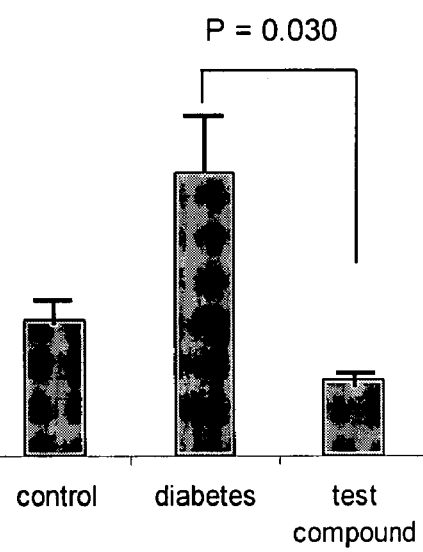

METHOD AND PHARMACEUTICAL COMPOSITIONS FOR TREATING OR INHIBITING RENAL DYSFUNCTIONS, DISEASES OR DISORDERS, PARTICULARLY IN DIABETIC PATIENTS

CROSS REFERENCE TO RELATED APPLICATIONS

This application claims priority from U.S. provisional patent application No. 60/523,106, filed Nov. 19, 2003. Priority is also claimed based on European patent application no. EP 03 10 4264.1, filed Nov. 18, 2003.

BACKGROUND OF THE INVENTION

The present invention relates to a novel use of benzazepine-N-acetic acid derivatives which contain an oxo-group in the α-position to the nitrogen atom and are substituted in position 3 by a 1-(carboxyalkyl)cyclopentylcarbonylamino radical, and/or of their salts and biolabile esters, and/or of physiologically acceptable solvates thereof in larger mammals and particularly in humans, especially human patients having diabetes, and to the production of pharmaceutical compositions and products suitable for the novel treatment.

Benzazepine-N-acetic acid derivatives which contain an oxo group in α-position to the nitrogen atom and are substituted in position 3 by a 1-(carboxyalkyl)cyclopentylcarbonylamino radical, and their salts and biolabile esters fall within the scope of the benzazepine, benzoxazepine and benzothiazepine-N-acetic acid derivatives which contain an oxo group in the α-position to the nitrogen atom and are substituted in position 3 by a 1-(carboxyalkyl)cyclopentylcarbonylamino radical and have NEP-inhibitory effects on the heart, as described in U.S. Pat. No. 5,677,297 (=DE 195 10 566 and EP 733,642). The benzazepine-N-acetic acid compounds used in the context of the present invention can be produced by the methods described in U.S. Pat. No. 5,677,297, which is incorporated herein by reference. Furthermore, the cause of the hypertension to be treated can have a wide variety of origins. Besides essential hypertension (primary hypertension), there are also forms of secondary hypertension which may occur as a result of various non-cardiac diseases, which may be also treated with the afore-mentioned benzazepine-N-acetic acid derivatives as described e.g. in U.S. Pat. No. 6,482,820 (=WO 00/48601 or EP 1154777).

The disclosure of U.S. Pat. No. 5,783,573 also embraces benzazepine-N-acetic acid derivatives, which contain an oxo-group in the α-position to the nitrogen atom and are substituted in position 3 by a 1-(carboxyalkyl)cyclopentylcarbonylamino radical, e.g. a reference is made to the use of such compounds in the improvement of gastrointestinal blood circulation (mesenteric blood flow). Reduced gastrointestinal blood flow can be caused by many different reasons, e.g. an increased vascular resistance of blood vessels which supply the gastrointestinal region or pathological changes in vascular function which can be connected to diabetes and/or cardiac diseases such as hypertensive cardiomyopathy.

Furthermore, in the state of the art the combined inhibition of neutral endopeptidase with angiotensin converting enzyme or endothelin converting enzyme in experimental diabetes is described by Tikkanen I. et al. (Journal of Hypertension 2002, 20: 707–714), however the described effects in relation to diabetes in the used streptozotocin-induced diabetic Sprague-Dawley rat model seem to be secondary to the blood pressure reduction by the compounds administered by Tikkanen I. et al.

SUMMARY OF THE INVENTION

The object of the invention is to provide a novel treatment for patients, in particular for patients subject to diabetic conditions, particularly for the treatment of certain serious renal complications of diabetes. The invention relates especially to the treatment and/or prophylaxis of those forms of diabetic complications which are related to the kidney function which may be impaired as a result of the diabetic disease. Hence, a most preferred objective of the invention is to improve the kidney function in diabetic patients or to provide a treatment and/or prophylaxis related to e.g. renal diseases which occur in the context of or as a complication of diabetes.

According to the invention compounds of the general formula I

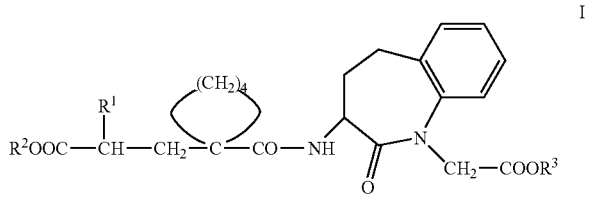

wherein
R1 stands for a phenyl-lower-alkyl group which can optionally be substituted in the phenyl ring by lower alkyl, lower alkoxy or halogen, or for a naphthyl-lower-alkyl group,
R2 means hydrogen or a group forming a biolabile ester, and
R3 means hydrogen or a group forming a biolabile group, and/or of a physiologically acceptable salt of the acids of formula I, and/or a physiologically acceptable solvate thereof, are used in a pharmaceutical composition for the treatment and/or prophylaxis of renal dysfunction, disease and/or disorder in a larger mammal or human patient, and preferably in a diabetic patient.

Where the substituents in the compounds of formula I are or contain lower alkyl or alkoxy groups, these can be straight-chain or branched and contain, in particular, 1 to 4, preferably 1 or 2, carbon atoms and are preferably methyl or methoxy. Where the substituents contain halogen, particularly suitable are fluorine, chlorine or bromine, preferably fluorine or chlorine.

In the radical R1 the lower alkylene chain can contain 1 to 4, preferably 1 or 2, carbon atoms. R1 in particular is an optionally substituted phenethyl group which can optionally be substituted one or more times by halogen, lower alkoxy or lower alkyl, or is a naphthylethyl group.

The compounds of formula I are optionally esterified dicarboxylic acid derivatives. Depending on the mode of administration, biolabile monoesters, particularly compounds in which R2 is a group forming a biolabile ester and R3 is hydrogen, or dicarboxylic acids are preferred, the latter being particularly suitable for i.v. administration.

Suitable R2 and R3 groups forming biolabile esters include lower alkyl groups, phenyl or phenyl-lower-alkyl groups which are optionally substituted in the phenyl ring by lower alkyl or by a lower alkylene chain bonded to two adjacent carbon atoms, dioxolanylmethyl groups which are optionally substituted in the dioxolane ring by lower alkyl, or C2–C6-alkanoyloxymethyl groups optionally substituted on the oxymethyl group by lower alkyl. Where the R2 or R3 group forming a biolabile ester is lower alkyl, this can be a preferably unbranched alkyl group with 1 to 4, preferably 2, carbon atoms. Where the group forming a biolabile ester is an optionally substituted phenyl-lower-alkyl group, its alkylene chain can contain 1 to 3, preferably 1, carbon atom. Where the phenyl ring is substituted by a lower alkylene chain, this can contain 3 to 4, particularly 3, carbon atoms. Phenyl, benzyl or indanyl are particularly suitable as phenyl-containing substituents R2 and/or R3. Where R2 and/or R3 are an optionally substituted alkanoyloxymethyl group, their alkanoyloxy group can contain 2 to 6, preferably 3 to 5, carbon atoms and is preferably branched and can be, for example, a pivaloyloxymethyl radical (=tert-butylcarbonyloxymethyl radical).

Suitable physiologically acceptable salts of dicarboxylic acids or monoesters of formula I include their alkali metal, alkaline earth metal or ammonium salts, for example sodium or calcium salts or salts with physiologically acceptable, pharmacologically neutral organic amines such as, for example, diethylamine or tert-butylamine.

The compounds of formula I contain two chiral (asymmetric) carbon atoms, namely the carbon atom which is in position 3 of the ring framework and carries the amide side-chain, and the carbon atom of the amide side-chain which carries the radical R1. The compounds can therefore exist in several optically active stereoisomeric forms or as a racemate. According to the present invention both the racemic mixtures and the isomerically pure compounds of formula I may be used.

It has now surprisingly been found that the group of compounds of formula I used according to the invention—besides their blood pressure-lowering effect in humans and larger mammals—may be also used for the treatment and/or prophylaxis of renal diseases, disorders or dysfunctions, in particular in patients subject to diabetic conditions. These patients often show renal complications, e.g. such as inappropriate or impaired function of the kidney. A very serious renal complication known in the context of diabetes is the so-called diabetic nephropathy. Impairment of the kidney function may result in undesired enhanced proteinuria and/or albumin secretion, which is a clear sign of renal pathological complication.

Accordingly, the compounds of formula I and their physiologically acceptable salts of the acids, and their biolabile esters or solvates are suitable not only for the treatment of any form of hypertension, e.g. for the treatment of essential or primary hypertension and certain forms of secondary hypertension which may have a wide variety of origins, but according to the findings of the present invention also for the treatment and/or prophylaxis of renal diseases, disorders or dysfunctions, in particular for the treatment and/or prophylaxis in patients subject to diabetic conditions. Preferably the compounds of formula I and their physiologically acceptable salts of the acids and their biolabile esters and/or solvates are suitable for the treatment and/or prophylaxis of renal complications of diabetes. Most preferably the compounds of formula I, including their salts of acids and their biolabile esters, are advantageously suitable for the treatment and/or prophylaxis of nephropatic conditions, e.g of diabetic nephropathy. The finding of the invention is rather surprising, because the experimental results shown and evaluated below lead to the conclusion that the compounds of formula I and their physiologically acceptable salts of the acids and their biolabile esters exhibit their nephroprotective properties completely independent of their blood pressure regulating properties which where already known in the state of the art. This implies that the beneficial effect is not related to the antihypertensive properties, but is subject to a different mechanism of action. Nevertheless, the compounds of formula I and their physiologically acceptable salts of the acids and their biolabile esters enable by their surprising pharmacological properties parallel treatment of hypertension and nephroprotecion through their beneficial effects on the kidney function.

In accordance with one aspect of the invention the compounds of formula I and their physiologically acceptable salts of the acids and their biolabile esters and/or solvates are used for the treatment and/or prophylaxis of a renal dysfunction, disease and/or disorder which is a nephropathy, preferably a nephropathy in diabetic patients (diabetic nephropathy). For example, the treatment and/or prophylaxis in this aspect of the invention is directed to the treatment and/or prophylaxis of proteinuria and/or urinary albumin excretion and/or renal scarring. There may be also an association with increased cardiovascular risks. Thus, according to the invention it is also beneficial to use compounds of formula I and their physiologically acceptable salts of the acids and their biolabile esters and/or solvates, in the treatment and/or prophylaxis of a renal dysfunction, disease and/or disorder in larger mammals or human patients showing enhanced cardiovascular risks, e.g. in patients with syndrome X. The invention also may be beneficial for the treatment and/or prophylaxis of patients with a renal dysfunction, disease and/or disorder, which patients are additionally hypertensive, obese, hyperglycemic and/or subject to a metabolic disorder.

The term diabetes is usually understood to mean diabetes mellitus, the so-called diabetic illness. In addition to other, e.g. secondary forms of diabetes that can occur as sequelae of other primary diseases, two main groups of disorders of carbohydrate metabolism are distinguished, i.e. type I diabetes due to insulin deficiency and type II diabetes due to reduced insulin effectiveness, the course of the disease depending on the type concerned, among other factors. Diabetes is furthermore a chronic disease with a variety of pathological manifestations and is accompanied, for example, by disorders of lipid metabolism, circulation and glucose metabolism. The typical symptoms of this disease include elevated blood sugar (hyperglycemia), excretion of sugar in the urine (glycosuria), tendency to infections and pruritus. Diabetes tends to be a progressive disorder and in many cases is also accompanied by various complications. Known complications include, for example, neurologic and vascular diseases.

The administration of the compounds of formula I and their physiologically acceptable salts of the acids and their biolabile esters and/or solvates for the treatment and/or prophylaxis of a renal dysfunction, disease and/or disorder is also beneficial for patients having in addition to such renal dysfunction, disease and/or disorder also hyperglycemia and/or a metabolic disorder, e.g. this administration is also suitable for patients having in addition a disorder of the glucose metabolism of varying origin which is associated with hyperglycemia, for example the occurrence of raised plasma glucose values as a result of increased glucose release and/or decreased metabolic glucose utilization, which can be associated with raised blood pressure, insulin resistance, glucose intolerance, type II diabetes and/or obesity.

The administration of the compounds of formula I and their physiologically acceptable salts of the acids and their biolabile esters and/or solvates for the treatment and/or prophylaxis of a renal dysfunction, disease and/or disorder is also beneficial for patients showing in addition syndrome X. Syndrome X is in particular a pattern of multiple anomalies, which are known or rare assumed to be causally combined. In a broader sense syndrome X patients usually show similar signs of dysfunction, disease or disorder, e.g. a mainly identical symptomatic pattern or symptoms of a manifest disease with a medical history of unknown, ambiguous or a vast variety of causes. In particular syndrome X is the clinical term for the combination of symptoms comprising insulin resistance, glucose intolerance, hyperinsulinemia, increased VLDL triglyceride levels, decreased HDL cholesterol and hypertension.

The administration of the compounds of formula I and their physiologically acceptable salts of the acids and their biolabile esters and/or solvates for the treatment and/or prophylaxis of a renal dysfunction, disease and/or disorder is also beneficial for patients who are additionally hypertensive. Hypertension (high blood pressure) means an increase in blood pressure beyond the normal level, which mainly becomes evident as arterial hypertension. Bearing in mind the etiology of the high blood pressure, a distinction is made between two basic forms, namely essential or primary hypertension on the one hand and the forms of secondary hypertension on the other. As a rule, essential hypertension is caused by increased flow resistance resulting from at first purely functional, later organic narrowing of the arterial circulation. Secondary or symptomatic hypertension, conversely, is an organ-related hypertension, i.e. provoked by the disease of an organ, which may take the form of endocrine, renal, pulmonary or cardiovascular hypertension, for example. The diseases causally responsible for secondary hypertension can be of a diverse nature, e.g. chronic obstructive airway diseases or chronic asthma. Normal circulation of the blood in the lungs of an adult person takes place at lower pressure and with low resistance. However, pre-existing chronic hypoxia, such as can occur, for example, in chronic obstructive airway diseases, leads to pulmonary arterial hypertension and to the remodeling of pulmonary arterioles (increased growth of vascular muscle cells) and of the right ventricle (increased growth of myocardial cells).

The administration of the compounds of formula I and their physiologically acceptable salts of the acids and their biolabile esters and/or solvates for the treatment and/or prophylaxis of a renal dysfunction, disease and/or disorder is also beneficial for patients who are obese. Obesity is known as the general increase of fat tissue caused by positive energy balance. Obesity is in particular a symptom of a metabolic disease.

For treatment and or prophylaxis according to the invention, the compounds of formula I and their physiologically acceptable salts of acids and their biolabile esters in conventional pharmaceutical compositions, can be administered by the oral, intravenous or transdermal route.

The compounds of formula I and their physiologically acceptable salts of acids and their biolabile esters, or their solvates in an effective renal protecting amount, together with conventional pharmaceutical adjuvants and/or carriers, can be contained in solid or liquid pharmaceutical compositions. Examples of solid preparations include orally administered preparations such as tablets, coated tablets, capsules, powders or granules, or also suppositories or patches (transdermal treatment systems). These solid preparations may contain pharmaceutically conventional inorganic and/or organic carriers, e.g. lactose, talc or starch, as well as pharmaceutically conventional adjuvants, for example lubricants or tablet disintegrants. Liquid preparations such as solutions, suspensions or emulsions of the active ingredients may contain the conventional diluents such as water, oils and/or suspending agents such as polyethylene glycols and similar agents. Other adjuvants may also be added, such as, for example, preservatives, taste corrigents and similar additives.

The active ingredients can be mixed and formulated with the pharmaceutical adjuvants and/or carriers in a known manner. For the preparation of solid pharmaceutical forms, the active ingredients can, for example, be mixed with the adjuvants and/or carriers in a conventional manner and granulated wet or dry. The granules or powder can be filled directly into capsules or compressed to form tablet cores in a conventional manner. These can optionally be coated in a known manner. Liquid compositions can be obtained in the form of solutions or suspensions by dissolving or dispersing the active ingredients and optionally other adjuvants in a suitable liquid carrier.

Therefore, one embodiment of the invention also pertains to a pharmaceutical composition comprising a therapeutically effective amount of at least one compound of formula I as defined above according to the present invention, and/or of at least one physiologically acceptable salt of an acid of formula I, and/or of at least one physiologically acceptable solvate thereof, which amount is therapeutically effective for the treatment and/or prophylaxis of renal dysfunction, disease and/or disorder in a larger mammal or a human patient, and preferably in a diabetic patient, and further comprising at least one pharmaceutically acceptable excipient or carrier, and optionally further pharmaceutical auxiliaries and/or adjuvants.

The pharmaceutical compositions for the treatment and/or inhibition of renal dysfunction, disease and/or disorder in a larger mammal or a human patient, and preferably in a diabetic patient, may be prepared according to the present invention by a process in which a therapeutically effective amount of at least one compound of formula I as defined above according to the present invention, and/or of at least one physiologically acceptable salt of an acid of formula I, and/or of at least one physiologically acceptable solvate thereof, is converted together with at least one pharmaceutically acceptable excipient or carrier, and optionally further pharmaceutical auxiliaries and/or adjuvants, into a pharmaceutical form found to be suitable.

In a further embodiment the invention also pertains to a pharmaceutical product and/or package containing as a medicament a pharmaceutical composition of a therapeutically effective amount of at least one compound of the general formula I as defined above according to the present invention, and/or at least one physiologically acceptable acid addition salt of an acid of formula I, and/or at least one physiologically acceptable solvate thereof, and further containing a label, leaflet and/or package insert indicating that said compound of the general formula I, said physiologically acceptable acid addition salt of an acid of formula I and/or said physiologically acceptable solvate thereof, may be administered for the treatment and/or prophylaxis of renal dysfunction, disease and/or disorder in a larger mammal or human patient, and preferably in a diabetic patient.

In yet a further embodiment, the invention also pertains to a method of treatment and/or prophylaxis of renal dysfunction, disease and/or disorder in a larger mammal or a human patient, and preferably in diabetic patients, wherein a pharmaceutical formulation comprising a therapeutically effective amount of at least one benzazepine-N-acetic acid derivative as defined according to the present invention, and/or at least one physiologically acceptable acid addition salt and/or at least one physiologically acceptable solvate thereof, is administered to said larger mammal or human patient.

Accordingly, in this embodiment of the invention the compounds of formula I and their physiologically acceptable salts of the acids and their biolabile esters and/or solvates are used for a method of treatment and/or prophylaxis of a renal dysfunction, disease and/or disorder which is a nephropathy, preferably a nephropathy in diabetic patients (diabetic nephropathy). For example, in this aspect the invention preferably is directed to the treatment and/or prophylaxis of proteinuria and/or urinary albumin excretion and/or renal scarring. In a further aspect of the invention the renal dysfunction, disease and/or disorder may be also associated with increased cardiovascular risks in certain patients. Thus, according to the invention it is also beneficial to use compounds of formula I and their physiologically acceptable salts of the acids and their biolabile esters and/or solvates, in the treatment and/or prophylaxis of a renal dysfunction, disease and/or disorder in larger mammals or human patients showing enhanced cardiovascular risks, e.g. in patients with syndrome X. Preferably the invention may be beneficial for the treatment and/or prophylaxis of patients with a renal dysfunction, disease and/or disorder, which patients are additionally hypertensive, obese, hyperglycemic and/or subject to a metabolic disorder.

The nephroprotective effect, in particular the beneficial effects in diabetic nephropathy, of the compounds of formula I according to the invention can be demonstrated in pharmacological tests in vivo in animal models, e.g. by measuring the effect of a test substance in relation to pharmacological indicators suitable for that purpose, e.g. by measuring proteinuria and/or albuminuria.

Description of Test Methods and Results:

In particular according to the present invention it was found in an animal model, as described further below in more detail, that inhibition of both neutral endopeptidase and endothelin converting enzyme reduces proteinuria and urinary albumin excretion in diabetic rats independent of blood pressure. Diabetic nephropathy is a serious complication of diabetes and is associated with poor prognosis and deteriorates to end-stage renal disease. Increased urinary excretion of protein and albumin are early clinical markers for diabetic renal disease and increased risk of cardiovascular disease. Diabetes causes activation of the renal endothelin system inducing renal scarring. As an example, the compound of formula I with the chemical name (3S,2'R)-3-{1-[2'-(ethoxycarbonyl)-4'-phenylbutyl]-cyclopentane-1-carbonylamino}-2,3,4,5-tetrahydro-2-oxo-1H-1-benzazepine-1-acetic-acid is an inhibitor of both neutral-endopeptidase (NEP) and endothelin-converting-enzyme (ECE) and inhibits endothelin (ET) formation. In rats with streptozotocin-induced diabetes, the effects on proteinuria of this compound of formula I (30 mg/kg/day, 18 weeks) were studied in comparison to control groups, e.g. compared to a vehicle-treated and non-diabetic control group. Drugs were administered orally with food.

Induction of Diabetes and Study Design:

All experiments were conducted in accordance with guidelines for the care and use of laboratory animals. Diabetes was induced in rats by a single tail vein injection of streptozotocin (60 mg/kg b.wt.), without insulin treatment, as recently described in Horcher et al., "Renal endothelin system in diabetes: inhibition and endothelin-A antagonism.", J. Cardiovasc. Pharmacol. 1998; 31: 492–495.

Diabetes was confirmed in streptozotocin treated rats by determining serum glucose concentrations. Only those rats were included having plasma glucose concentrations of >15 mmol/l (hyperglycemic rats, diabetic rats). Three groups of rats were investigated with n 7 to 11 per group:

1) non-diabetic rats control group;
2) diabetic rats control group, vehicle treated;
3) treated diabetic rats group: with test compound of formula I ((3S,2'R)-3-{1-[2'-(ethoxycarbonyl)-4'-phenylbutyl]-cyclopentane-1-carbonylamino}-2,3,4,5-tetrahydro-2-oxo-1H-1-benzazepine-1-acetic-acid), 30 mg/kg/day for 18 weeks.

Urinary protein concentration in urine was measured with a pyrogallol red-molybdate complex reagent (analytic test kit) in an automated analyzer, e.g. Hitachi 717; See also: Watanabe N, Kamei S, Ohkubo A, Yamanaka M, Ohsawa S, Makino K, Tokuda, K: "Urinary protein as measured with a pyrogallol red-molybdate complex reagent (analytic test kit) in an Hitachi 726 automated analyzer.", Clin. Chem. 1986, 32: 1551–1554.

Urinary albumin excretion was determined by an enzyme-linked immunosorbent assay. Rabbit anti-rat albumin was diluted 10,000 and 600 times, respectively. Heat-inactivated normal rabbit serum was used as a blocker. Standard curves were linear between 0.3 and 40 ng of albumin per well. Addition of known standard amounts of albumin to urine resulted in 97% recovery of added albumin (See also: Horcher et al., Nephron 2001; 87: 161–169; "Effects of Endothelin Receptor Antagonists on the Progression of Diabetic Nephropathy").

Glomerular filtration rate was calculated by the endogeneous creatinine clearance. It was observed that administering a compound of formula I as defined above improved the overall glomerular filtration rate.

The experiment performed according to the present invention over 18 weeks of treatment provided the following results which are detailed in Table I, and FIGS. 1 and 2. In the context of the present invention, the most important data to be considered are the mean blood pressure (BP; tail-cuff plethysmography), the protein and albumin excretion (mean values, standard deviations) in urine which was collected in metabolic cages over 24 h, and number (n) of animals in each group regarding non-diabetic controls, diabetic vehicle treated controls (=placebo) and test compound treated group.

At baseline, serum glucose and blood pressure were similar in both diabetic groups. Compared to vehicle, the test compound of formula I had no effect on these parameters during the treatment period. After 18 weeks treatment, urinary protein and albumin excretion were measured. Protein excretion in the vehicle-treated group was about 18 mg/24 h; in the group which had received the compound of formula I it was about 4.8 mg/24 h (p=0.03 versus vehicle). Albumin excretion in the vehicle-group was about 0.5 mg/24 h, and in the which had received the compound of formula I it was about 0.1 mg/24 h (p=0.04). Compared to vehicle, plasma concentrations of ET-1, bigET-1 and angiotensin-II were unchanged by compound of formula I. No side-effects were observed with test compound of formula I treatment. From the experiments it can be concluded that test compound of formula I decreases protein and albumin excretion in diabetic rats independent of blood pressure. From the results it may be concluded that the compounds of formula I exert a primary effect on end-organ disease.

TABLE I

Inhibition of both neutral endopeptidase and endothelin converting enzyme reduces proteinuria and urinary albumin excretion in diabetic rats independent of blood pressure. Test data after 18 weeks of treatment. In all three groups no major effects on blood pressure were observed during the treatment period.

| Parameter | 1) Control Group non-diabetic rats | 2) Control Group diabetic rats vehicle treated | 3) Test Group diabetic rats |
|---|---|---|---|
| Blood Pressure (mmHg) | | | |
| mean value | 111 | 126 | 129 |
| number of animals (n) | 10 | 7 | 8 |
| standard deviation (SD) | 23.36 | 14.00 | 12.79 |
| Heart Rate (beats/min) | | | |
| mean value | 408 | 297 | 280 |
| number of animals (n) | 10 | 7 | 8 |
| standard deviation (SD) | 35.83 | 38.02 | 25.73 |
| Body Weight (g) | | | |
| mean value | 401.2 | 294 | 252.7 |
| number of animals (n) | 11 | 7 | 8 |
| standard deviation (SD) | 41.82 | 39.29 | 55.71 |
| Proteinuria (mg/24 h) | | | |
| mean value | 8.72382 | 17.98814 | 4.81913 |
| number of animals (n) | 11 | 7 | 8 |
| standard deviation (SD) | 5.81 | 12.36 | 2.77 |
| Albuminuria (mg/24 h) | | | |
| mean value | 0.07204 | 0.49509 | 0.09874 |
| number of animals (n) | 11 | 7 | 7 |
| standard deviation (SD) | 0.11 | 0.41 | 0.08 |
| Glomerular Filtration Rate (ml/min), final | | | |
| mean value | 2.66614 | 1.69559 | 2.01351 |
| number of animals (n) | 11 | 7 | 8 |
| standard deviation (SD) | 1.17 | 0.82 | 0.95 |
| Glucose, final (mg/dl) | | | |
| mean value | 127.18 | 504.71 | 560.33 |
| number of animals (n) | 11 | 7 | 6 |
| standard deviation (SD) | 7.08 | 155.89 | 63.09 |

BRIEF DESCRIPTION OF THE DRAWINGS

FIG. 1:
Protein excretion after 12 weeks (FIG. 1A) and 18 weeks (FIG. 1B).
Protein excretion after 12 and 18 weeks oral treatment of diabetic rats with 30 mg/kg/day of test compound; values are means±S.E.M. (standard error of the mean), n 7 to 11 animals.

Figure 2:
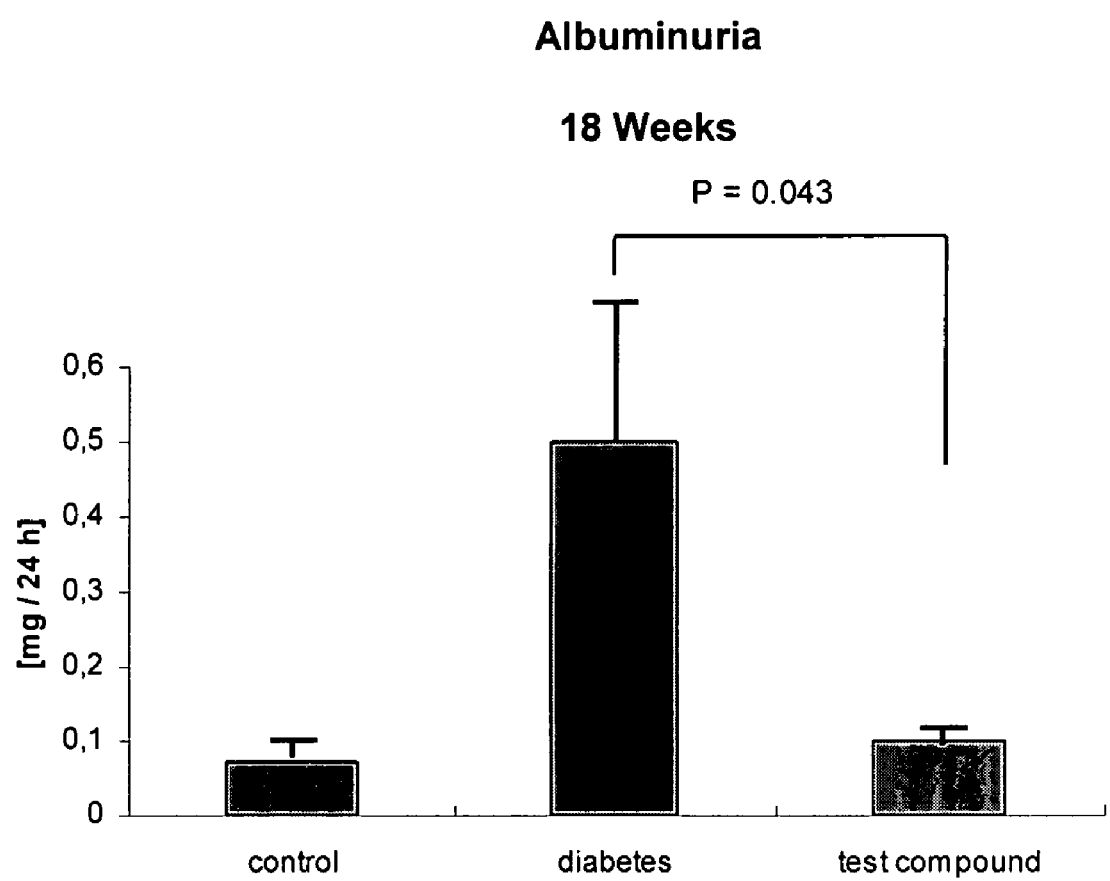
FIG. 2:
Albumin excretion after 18 weeks.
Albumin excretion after 1 18 weeks oral treatment of diabetic rats with 30 mg/kg/day of test compound; values are means±S.E.M. (standard error of the mean), n 7 to 11 animals.

The experimental data shows that in particular proteinuria and also the albuminuria are reduced. These effects mean that administration of a compound of formula I can provide positive effects regarding renal remodeling, e.g. there are positive effects on interstitial matrix content, which are in accordance with the reduced proteinuria and albuminuria. In particular the compounds adiministered according to the invention show antifibrotic effects, e.g. treated animals show less fibrosis. Hence, in addition to investigation of the glomerular filtration rate, urinary albumin and total protein excretion, also histological investigations, e.g. the morphometric examination of the kidneys, supports the surprisingly positive nephroprotective effect of the compounds of formula I as defined above according to the present invention. Thus, surprisingly the compounds of formula I as defined according to the present invention show substantial renal protective effects.

Histological investigations are usually performed in streptozotocin-induced diabetic rats by administration of a test compound, and then analyzing the effects on the expression of interstitial and glomerular collagen type I, III and IV as well as on fibronectin and laminin by quantitative immunohistochemistry using a computer-aided image analysis system. Global glomerular matrix deposition is analyzed after PAS staining. A more detailed description of the general methodology that may be employed for histological investigations is given by B. Horcher et al. in Nephron 2001; 87:161–169 ("Effects of Endothelin Receptor Antagonists on the Progression of Diabetic Nephropathy").

The effects observed according to the present invention are primary, e.g. direct effects, meaning that these effects are independent of the blood pressure lowering effects of the compounds of the formula I as defined above according to the present invention. In particular, the results of the experiments in accordance with the present invention show that the compounds of formula I administered according to the invention are beneficially suited for long-term treatment and/or prophylaxis.

In view of their nephroprotective effects described above, the compounds of formula I and their salts and biolabile esters, and/or solvates are suitable as pharmaceutical compositions for larger mammals and humans for the treatment of renal dysfunction, disease and/or disorder which is a nephropathy, preferably a nephropathy in diabetic patients (diabetic nephropathy), and/or pathologic conditions as described above more in detail.

The compounds used according to the invention are particularly suitable for the treatment of those forms of diabetic nephropathy which may occur in association with cardiovascular risks, e.g. in patients with syndrome X. Preferably compounds used according to the invention may be beneficial for the treatment and/or prophylaxis of patients with a renal dysfunction, disease and/or disorder, which patients are in addition hypertensive, obese, hyperglycemic and/or subject to a metabolic disorder. The compounds used according to the invention thereby offer an advantageous direct approach to the treatment and/or prevention of renal dysfunction, disease and/or disorder, in particular, nephropathy in diabetic patients, in particular independently from systemic blood pressure.

For this purpose, dicarboxylic acids of formula I and their salts are used appropriately in pharmaceutical forms for parenteral, particularly i.v., administration, and mono- or diesters of formula I are used appropriately in orally administered pharmaceutical forms. The doses to be used can differ between individuals and naturally vary according to the nature of the condition to be treated, the substance used and the form of administration. For example, parenteral formulations will generally contain less active substance than oral preparations. However, pharmaceutical forms with active substance content of 1 to 200 mg per individual dose are generally suitable for administration to larger mammals, particularly humans. The compounds of formula I, including their salts of acids and their biolabile esters, can be administered for this purpose in pharmaceutical compositions both for immediate and also delayed and/or controlled release of active substance.

The following examples are intended to illustrate the invention in further detail without restricting its scope in any way.

The following examples 1 and 2 describe pharmaceutical compositions according to the invention, which contain an active substance of formula I, and the production of such pharmaceutical compositions. The compounds of formula I used according to the invention can be produced for this purpose by the methods described in the previously mentioned U.S. Pat. No. 5,677,297, which is incorporated herein by reference. Example 3 names preferred embodiments for use according to the invention.

EXAMPLE 1

Tablets containing (3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetic acid.

Tablets with the following composition per tablet were produced:

| | |
|---|---|
| (3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetic acid | 20 mg |
| Maize starch | 60 mg |
| Lactose | 135 mg |
| Gelatin (as 10% solution) | 6 mg |

The active substance, the maize starch and the lactose were thickened with the 10% gelatin solution. The paste was comminuted, and the resulting granules were placed on a suitable sheet and dried at 45° C. The dried granules were fed through a crushing machine and mixed with the following further adjuvants in a mixer:

| | |
|---|---|
| Talc | 5 mg |
| Magnesium stearate | 5 mg |
| Maize starch | 9 mg | and then compressed to form tablets of 240 mg.

EXAMPLE 2

Injection solution containing (3S,2'R)-3-[1-(2'-carboxy-4'-phenylbutyl)cyclopentane-1-carbonylamino]-2,3,4,5-tetrahydro-2-oxo-1H-1-benzazepine-1-acetic acid.

An injection solution with the following composition per 5 ml was produced:

| | |
|---|---|
| (3S,2'R)-3-[1-(2'-carboxy-4'-phenylbutyl)cyclopentane-1-carbonylamino]-2,3,4,5-tetrahydro-2-oxo-1H-1-benzazepine-1-acetic acid | 10 mg |
| $Na_2HPO_4 \cdot 7H_2O$ | 43.24 mg |
| $NaH_2PO_4 \cdot 2H_2O$ | 7.72 mg |
| NaCl | 30.0 mg |
| purified water | 4948.0 mg |

The solids were dissolved in water, the solution was sterilized and filled into ampoules in 5 ml portions.

EXAMPLE 3

Preferred embodiments of formula I for use according to the invention for the production of pharmaceutical compositions for the treatment of hypertension, particularly for the treatment of secondary forms of hypertension such as e.g. pulmonary hypertension, are for example (including the salts of acids):

3-{1-[2'-(ethoxycarbonyl)-4'-phenylbutyl]cyclopentane-1-carbonylamino}-2,3,4,5-tetrahydro-2-oxo-1H-1-benzazepine-1-acetic-acid-tert-butylester.

3-{1-[2'-(ethoxycarbonyl)-4'-phenylbutyl]cyclopentane-1-carbonylamino}-2,3,4,5-tetrahydro-2-oxo-1H-1-benzazepine-1-acetic-acid.

(3S,2'R)-3-{1-[2'-ethoxycarbonyl)-4'-phenylbutyl]cyclopentane-1-carbonylamino}-2,3,4,5-tetrahydro-2-oxo-1H-1-benzazepine-1-acetic-acid-tert-butylester.

(3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetic-acid.

(3S,2'R)-3-{1-[2'-(carboxy-4'-phenylbutyl]cyclopentane-1-carbonylamino}-2,3,4,5-tetrahydro-2-oxo-1H-1-benzazepine-1-acetic-acid.

3-{1-[2'-(tert-butoxycarbonyl)-4'-phenylbutyl]cyclopentane-1-carbonylamino}-2,3,4,5-tetrahydro-2-oxo-1H-1-benzazepine-1-acetic-acid-tert-butylester.

3-[1-(2'-carboxy-4'-phenylbutyl)cyclopentane-1-carbonylamino]-2,3,4,5-tetrahydro-2-oxo-1H-1-benzazepine-1-acetic-acid.

3-{1-[2'-(tert-butoxycarbonyl)-4'-phenylbutyl]cyclopentane-1-carbonylamino}-2,3,4,5-tetrahydro-2-oxo-1H-1-benzazepine-1-acetic-acid-benzylester.

3-[1-(2'-carboxy-4'-phenylbutyl)cyclopentane-1-carbonylamino]-2,3,4,5-tetrahydro-2-oxo-1H-1-benzazepine-1-acetic-acid-benzylester.

3-{1-[2'-(tert-butylcarbonyloxymethoxycarbonyl)-4'-phenylbutyl]cyclopentane-1-carbonylamino}-2,3,4,5-tetrahydro-2-oxo-1H-1-benzazepine-1-acetic-acid-benzylester.

3-{1-[2'-(pivaloyloxymethoxycarbonyl)-4'-phenylbutyl]cyclopentane-1-carbonylamino}-2,3,4,5-tetrahydro-2-oxo-1H-1-benzazepine-1-acetic-acid.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating or inhibiting a nephropathy which comprises at least one of proteinuria, urinary albumin excretion or renal scaring in a human patient, said method comprising administering to said patient a pharmaceutically effective amount of a benzazepine-N-acetic acid derivative corresponding to formula I

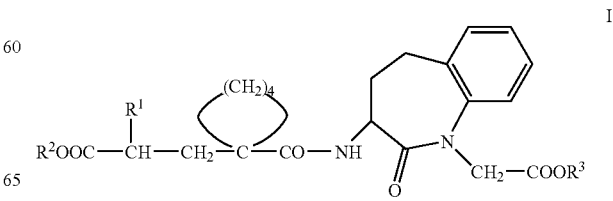

wherein
- R1 stands for a phenyl-lower-alkyl group which can optionally be substituted in the phenyl ring by lower alkyl, lower alkoxy or halogen, or for a naphthyl-lower-alkyl group,
- R2 stands for hydrogen or a group forming a biolabile ester, and
- R3 stands for hydrogen or a group forming a biolabile group, or a physiologically acceptable salt or solvate thereof.

2. A method according to claim 1, wherein said patient is a diabetic patient.

3. A method according to claim 1, wherein said nephropathy is a diabetic nephropathy.

4. A method according to claim 1, wherein said patient is a patient which exhibits enhanced cardiovascular risks.

5. A method according to claim 4, wherein said patient is a patient suffering from syndrome X.

6. A method according to claim 4, wherein said patient is a patient with a renal dysfunction, disease or disorder, and additionally suffers from at least one condition selected from the group consisting of hypertension, obesity, hyperglycemia and metabolic disorders.

7. A method according to claim 1, wherein R2 or R3 stands for a group forming a biolabile ester.

8. A method according to claim 7, wherein the group forming a biolabile ester is:

a lower alkyl group; or a phenyl or phenyl-lower-alkyl group, which is optionally substituted in the phenyl ring by lower alkyl or by a lower alkylene chain bonded to two adjacent carbon atoms; or a dioxolanylmethyl group, which is optionally substituted in the dioxolane ring by lower alkyl, or a C2–C6-alkanoyloxymethyl group, optionally substituted on the oxymethyl group by lower alkyl.

9. A method according to claim 8, wherein said group forming a biolabile ester is a phenyl, benzyl or indanyl group.

10. A method according to claim 8, wherein said group forming a biolabile ester is a (2,2-dimethyl-1,3-dioxolane-4-yl)methyl group.

11. A method according to claim 1, wherein R2 is a group forming a biolabile ester, and R3 is hydrogen.

12. A method according to claim 1, wherein said compound comprises (3S,2'R)-3-{1-[2'-(ethoxycarbonyl)-4'-phenylbutyl]-cyclopentane-1-carbonylamino}-2,3,4,5-tetrahydro-2-oxo-1H-1-benzazepine-1-acetic-acid or a physiologically acceptable salt thereof.

* * * * *